United States Patent
Sunkara et al.

(10) Patent No.: US 8,409,596 B2
(45) Date of Patent: *Apr. 2, 2013

(54) DEODORANT COMPOSITIONS

(75) Inventors: Hari Babu Sunkara, Hockessin, DE (US); Raja Hari Poladi, Bear, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/344,237

(22) Filed: Jan. 5, 2012

(65) Prior Publication Data

US 2012/0107260 A1    May 3, 2012

Related U.S. Application Data

(62) Division of application No. 11/869,056, filed on Oct. 9, 2007, now Pat. No. 8,114,423.

(51) Int. Cl.
*A61K 8/02* (2006.01)
*A61K 31/74* (2006.01)
*C07C 43/02* (2006.01)
*C08G 65/34* (2006.01)

(52) U.S. Cl. ........ 424/401; 568/619; 528/425; 528/272; 525/437; 525/444; 424/78.02

(58) Field of Classification Search .................. 424/401, 424/78.02; 568/619; 528/425, 272; 525/437, 525/444

See application file for complete search history.

(56) References Cited

U.S. PATENT DOCUMENTS

| | | | |
|---|---|---|---|
| 3,755,560 A | 8/1973 | Dickert et al. | |
| 4,254,105 A | 3/1981 | Fukuda | |
| 4,421,769 A | 12/1983 | Dixon et al. | |
| 4,636,525 A | 1/1987 | Ochiai et al. | |
| 5,256,396 A | 10/1993 | Piechota, Jr. | |
| 5,633,362 A | 5/1997 | Nagarajan et al. | |
| 5,650,143 A | 7/1997 | Bergmann et al. | |
| 5,686,276 A | 11/1997 | Laffend et al. | |
| 5,821,092 A | 10/1998 | Nagarajan et al. | |
| 6,270,459 B1 | 8/2001 | Konofagou et al. | |
| 6,608,168 B1 | 8/2003 | Ng | |
| 6,977,291 B2 | 12/2005 | Sunkara et al. | |
| 2003/0007939 A1 | 1/2003 | Murad | |
| 2004/0030095 A1 | 2/2004 | Sunkara et al. | |
| 2004/0105873 A1 | 6/2004 | Gupta | |
| 2004/0225161 A1 | 11/2004 | Sunkara et al. | |
| 2004/0241200 A1 | 12/2004 | Winn et al. | |
| 2004/0260125 A1 | 12/2004 | Seapan et al. | |
| 2005/0020805 A1 | 1/2005 | Sunkara et al. | |
| 2005/0069997 A1 | 3/2005 | Adkesson et al. | |
| 2006/0165623 A1 | 7/2006 | Workman et al. | |
| 2007/0185003 A1 | 8/2007 | Iavarone et al. | |
| 2007/0269392 A1 | 11/2007 | Sunkara | |
| 2008/0108845 A1 | 5/2008 | Sunkara et al. | |

FOREIGN PATENT DOCUMENTS

EP    1283031 A2    2/2003
WO    2007136586 A2    11/2007

OTHER PUBLICATIONS

U.S. Appl. No. 11/593,954, filed Nov. 7, 2006, Sunkara et al.
Buchmann, "Main Cosmetic Vehicles", Handbook of Cosmetic Science and Technology, $2^{nd}$ Edition, edited by Paye et al., 2005, pp. 99-123.
Currie, "Source Apportionment of Atmospheric Particles", Buffle et al., Editors, 1 of vol. 1 of the IUPAC Environmental Analytical Cnemistry Series (Lewis Publishers, Inc.), 1992, pp. 3-74.
Hsieh, "Division S-3—Soil Microbiology & Biochemistry, Pool Size and Mean Age of Stable Soil Organic Carbon in Cropland", Soil Sci. Soc. Am. J., vol. 56, 1992, pp. 460-464.
Hoffmann et al., "Heat-Induced Aggregation of B-Lactoglobulin: Role of the Free Thiol Group and DisulfideBonds", J. Agric. Food Chem., 45, 1997, pp. 2942-2948.
International Search Report, PCT International Application No. PCT/US2007/021607, Jun. 29, 2009.
International Preliminary Report on Patentability, PCT International Application PCT/US2007/021607, Mailed Apr. 22, 2010.

*Primary Examiner* — Savitha Rao

(57) ABSTRACT

This invention relates to deodorant compositions containing polytrimethylene ether glycol homo- and copolymers and/or polytrimethylene glycol ester(s) in a variety of physical forms. In at least one embodiment, the polytrimethylene ether glycol homo- and copolymers and/or polytrimethylene glycol ester(s) can be made from monomers (e.g., 1,3-propanediol) obtained from renewable resources, and can thus be more environmentally friendly than conventional deodorant compositions in terms of manufacture, use and disposal.

16 Claims, No Drawings

DEODORANT COMPOSITIONS

FIELD OF THE INVENTION

This invention relates to deodorant compositions containing polytrimethylene ether glycol homo- and copolymers and/or polytrimethylene glycol ester(s) in a variety of physical forms. In some embodiments, the polytrimethylene ether glycol homo- and copolymers and/or polytrimethylene glycol ester(s) are derived predominantly from monomers (e.g., 1,3-propanediol) obtained from renewable resources, and are thus more environmentally friendly in terms of manufacture, use and disposal.

BACKGROUND

There are a large number of deodorant products available, most of which are in the form of solid sticks, sprays, solutions, creams, ointments, lotions, gels or emulsions. The ingredients in the formulated products in general serve as emollients, humectants, moisturizers, emulsifiers, lubricants, antimicrobials, cosmetics, fragrances, rheology modifiers, etc. Some of the products are solvent-based and others are water-based.

Most often deodorant products contain an active ingredient incorporated in a delivery vehicle. The desired effect of a deodorant product is achieved either by the deodorant active ingredients or by the vehicle itself at the site of application, in most cases on the skin.

The major types of deodorant vehicles most frequently fall into the following categories: (a) solutions; (b) emulsions, both oil-in-water and water-in-oil, including, for example lotions and creams); (c) suspensions; (d) gels; and (e) solids (including semi-solids) including (for example) stick products. An extensive discussion of personal care and cosmetic vehicles is found in *Handbook of Cosmetic Science and Technology*, Second Edition, edited by M Paye, A. O. Barel and H. I. Maibach, pages 99-123 (2005).

The majority of ingredients used in deodorant products, including polyols and silicones, are synthetic and are derived from petrochemical sources. The recent trend of the industry is to provide products to consumers that are natural and reduced in petroleum-based product content.

Co-owned U.S. application Ser. No. 11/801,872, filed May 11, 2007, entitled "PERSONAL CARE COMPOSITIONS", discloses a personal care composition comprising an effective amount of at least one active personal care ingredient in a vehicle, wherein the vehicle comprises from about 0.1 to 100% by weight, based on the weight of the vehicle, of polytrimethylene ether glycol. Specific molecular weight ranges for polytrimethylene ether glycol are not disclosed, and preferred amounts of polytrimethylene ether glycol are 50 weight percent or less.

Certain mono- and diesters of polytrimethylene ether glycol ("PO3G esters") have properties that make them useful in a variety of fields, as disclosed in commonly owned U.S. application Ser. No. 11/593,954, filed Nov. 7, 2006, entitled "POLYTRIMETHYLENE ETHER GLYCOL ESTERS".

US Patent Publication 2006/0165623 A1 describes a natural deodorant system and a natural system for topical and systemic delivery of active ingredients.

U.S. Pat. No. 5,650,143 discloses a deodorant cosmetic stick product which has a translucent or transparent light transmitting appearance, and a content of ingredients such as propylene glyol, sodium stearate, dimethicone copolyol, Triclosan, Pentadoxynol-200, and water.

US Patent Publication 2004/0241200 A1 describes personal care products, including deodorants, not containing tetramer and/or pentamer cyclomethicone fluids, but including at least one neopentyl polyol polyester derived from neopentyl glycol, at least one isoparaffin, and a personal care formulation.

There is a need for products having reduced environmental impact. There is also an environmental advantage for manufacturers to provide products derived from renewable sources. There thus exists a need for deodorant products comprising ingredients not derived from petroleum but from renewable resources. In addition, there is a need for ingredients and products that are environmentally friendly in respect to their manufacturing processes, their uses and their disposal.

SUMMARY OF THE INVENTION

One aspect of the present invention is a deodorant composition comprising an effective amount of at least one active deodorant ingredient in a vehicle, wherein the vehicle comprises polytrimethylene ether glycol.

Another aspect of the present invention is a deodorant composition comprising a polytrimethylene ether glycol ester and at least one active deodorant ingredient.

Another aspect of the present invention is a deodorant composition comprising an effective amount of at least one active deodorant ingredient in a vehicle, wherein the vehicle comprises polytrimethylene ether glycol ester(s).

Another aspect of the present invention is a deodorant composition comprising an effective amount of at least one active deodorant ingredient in a vehicle, wherein the vehicle comprises from about 5 to 85 percent by weight, based on the weight of the vehicle, of polytrimethylene ether glycol.

In some preferred embodiments, the deodorant compositions comprise greater than about 70 percent renewably sourced ingredients, based on the total weight of the composition.

DETAILED DESCRIPTION OF THE PREFERRED EMBODIMENTS

All publications, patent applications, patents and other references mentioned herein, if not otherwise indicated, are incorporated by reference herein for all purposes as if fully set forth.

Unless otherwise defined, all technical and scientific terms used herein have the same meaning as commonly understood by one of ordinary skill in the art to which this invention belongs. In case of conflict, the present specification, including definitions, will control.

Except where expressly noted, trademarks are shown in upper case.

Unless stated otherwise, all percentages, parts, ratios, etc., are by weight.

When an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

When the term "about" is used in describing a value or an end-point of a range, the disclosure should be understood to include the specific value or endpoint referred to.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Use of "a" or "an" are employed to describe elements and components of the invention. This is done merely for convenience and to give a general sense of the invention. This description should be read to include one or at least one and the singular also includes the plural unless it is obvious that it is meant otherwise.

The materials, methods, and examples herein are illustrative only and, except as specifically stated, are not intended to be limiting. Although methods and materials similar or equivalent to those described herein can be used in the practice or testing of the present invention, suitable methods and materials are described herein.

Polytrimethylene Ether Glycol (PO3G)

The deodorant compositions of the invention generally include from about 10 to about 90 wt % by weight of polytrimethylene ether glycol based on the weight of the deodorant composition. In certain preferred embodiments, the compositions preferably include from about 10 to about 85% by weight, and still more preferably from about 10 to about 70% by weight, of polytrimethylene ether glycol based on the weight of the deodorant composition.

Polytrimethylene ether glycols are oligomers and polymers in which at least 50% of the repeating units are trimethylene ether units. More preferably from about 75% to 100%, still more preferably from about 90% to 100%, and even more preferably from about 99% to 100%, of the repeating units are trimethylene ether units.

Polytrimethylene ether glycols are preferably prepared by polycondensation of monomers comprising 1,3-propanediol, thus resulting in polymers or copolymers containing —$(CH_2CH_2CH_2O)$— linkage (e.g, trimethylene ether repeating units). As indicated above, at least 50% of the repeating units are trimethylene ether units.

In addition to the trimethylene ether units, lesser amounts of other units, such as other polyalkylene ether repeating units, may be present also. In the context of this disclosure, the term "polytrimethylene ether glycol" encompasses polytrimethylene ether glycol made from essentially pure 1,3-propanediol, as well as those oligomers and polymers (including those described below) containing up to about 50% by weight of comonomers.

The 1,3-propanediol employed for preparing the polytrimethylene ether glycols may be obtained by any of the various well known chemical routes or by biochemical transformation routes. Most preferably, the 1,3-propanediol is obtained biochemically from a renewable source ("biologically-derived" 1,3-propanediol).

The most preferred source of 1,3-propanediol is via a fermentation process using a renewable biological source. As an illustrative example of a starting material from a renewable source, biochemical routes to 1,3-propanediol (PDO) have been described that utilize feedstocks produced from biological and renewable resources such as corn feed stock. For example, bacterial strains able to convert glycerol into 1,3-propanediol are found in the species *Klebsiella, Citrobacter, Clostridium*, and *Lactobacillus*. The technique is disclosed in several patents, including U.S. Pat. No. 5,633,362, U.S. Pat. No. 5,686,276 and U.S. Pat. No. 5,821,092 (the disclosures of which are incorporated by reference herein for all purposes as if fully set forth). For example, U.S. Pat. No. 5,821,092 discloses, inter alia, a process for the biological production of 1,3-propanediol from glycerol using recombinant organisms. The process incorporates *E. coli* bacteria, transformed with a heterologous pdu diol dehydratase gene, having specificity for 1,2-propanediol. The transformed *E. coli* is grown in the presence of glycerol as a carbon source and 1,3-propanediol is isolated from the growth media. Since both bacteria and yeasts can convert glucose (e.g., corn sugar) or other carbohydrates to glycerol, the processes disclosed in these publications provide a rapid, inexpensive and environmentally responsible source of 1,3-propanediol monomer.

The biologically-derived 1,3-propanediol, such as produced by the processes described and referenced above, contains carbon from the atmospheric carbon dioxide incorporated by plants, which compose the feedstock for the production of the 1,3-propanediol. In this way, the biologically-derived 1,3-propanediol preferred for use in the context of the present invention contains only renewable carbon, and not fossil fuel-based or petroleum-based carbon. The polytrimethylene ether glycol and deodorant compositions of the present invention utilizing the biologically-derived 1,3-propanediol, therefore, have less impact on the environment as the 1,3-propanediol used in the compositions does not deplete diminishing fossil fuels and, upon degradation, releases carbon back to the atmosphere for use by plants once again. Thus, the compositions present invention can be characterized as more natural and having less environmental impact than similar compositions comprising petroleum based glycols.

The biologically-derived 1,3-propanediol, and polytrimethylene ether glycols, may be distinguished from similar compounds produced from a petrochemical source or from fossil fuel carbon by dual carbon-isotopic finger printing. This method usefully distinguishes chemically-identical materials, and apportions carbon in the copolymer by source (and possibly year) of growth of the biospheric (plant) component. The isotopes, $^{14}C$ and $^{13}C$, bring complementary information to this problem. The radiocarbon dating isotope ($^{14}C$), with its nuclear half life of 5730 years, clearly allows one to apportion specimen carbon between fossil ("dead") and biospheric ("alive") feedstocks (Currie, L. A. "Source Apportionment of Atmospheric Particles," *Characterization of Environmental Particles*, J. Buffle and H. P. van Leeuwen, Eds., 1 of Vol. I of the IUPAC Environmental Analytical Chemistry Series (Lewis Publishers, Inc) (1992) 3-74). The basic assumption in radiocarbon dating is that the constancy of $^{14}C$ concentration in the atmosphere leads to the constancy of $^{14}C$ in living organisms. When dealing with an isolated sample, the age of a sample can be deduced approximately by the relationship $$t=(-5730/0.693)\ln(A/A_0)$$

where t=age, 5730 years is the half-life of radiocarbon, and A and $A_0$ are the specific $^{14}C$ activity of the sample and of the modern standard, respectively (Hsieh, Y., *Soil Sci. Soc. Am J.*, 56, 460, (1992)). However, because of atmospheric nuclear testing since 1950 and the burning of fossil fuel since 1850, $^{14}C$ has acquired a second, geochemical time characteristic.

Its concentration in atmospheric $CO_2$, and hence in the living biosphere, approximately doubled at the peak of nuclear testing, in the mid-1960s. It has since been gradually returning to the steady-state cosmogenic (atmospheric) baseline isotope rate ($^{14}C/^{12}C$) of ca. $1.2 \times 10^{-12}$, with an approximate relaxation "half-life" of 7-10 years. (This latter half-life must not be taken literally; rather, one must use the detailed atmospheric nuclear input/decay function to trace the variation of atmospheric and biospheric $^{14}C$ since the onset of the nuclear age.) It is this latter biospheric $^{14}C$ time characteristic that holds out the promise of annual dating of recent biospheric carbon. $^{14}C$ can be measured by accelerator mass spectrometry (AMS), with results given in units of "fraction of modern carbon" ($f_M$). $f_M$ is defined by National Institute of Standards and Technology (NIST) Standard Reference Materials (SRMs) 4990B and 49900, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), $f_M \approx 1.11$ The stable carbon isotope ratio ($^{13}C/^{12}C$) provides a complementary route to source discrimination and apportionment. The $^{13}C/^{12}C$ ratio in a given biosourced material is a consequence of the $^{13}C/^{12}C$ ratio in atmospheric carbon dioxide at the time the carbon dioxide is fixed and also reflects the precise metabolic pathway. Regional variations also occur. Petroleum, $C_3$ plants (the broadleaf), $C_4$ plants (the grasses), and marine carbonates all show significant differences in $^{13}C/^{12}C$ and the corresponding $\delta$ $^{13}C$ values. Furthermore, lipid matter of $C_3$ and $C_4$ plants analyze differently than materials derived from the carbohydrate components of the same plants as a consequence of the metabolic pathway. Within the precision of measurement, $^{13}C$ shows large variations due to isotopic fractionation effects, the most significant of which for the instant invention is the photosynthetic mechanism. The major cause of differences in the carbon isotope ratio in plants is closely associated with differences in the pathway of photosynthetic carbon metabolism in the plants, particularly the reaction occurring during the primary carboxylation, i.e., the initial fixation of atmospheric $CO_2$. Two large classes of vegetation are those that incorporate the "$C_3$" (or Calvin-Benson) photosynthetic cycle and those that incorporate the "$C_4$" (or Hatch-Slack) photosynthetic cycle. $C_3$ plants, such as hardwoods and conifers, are dominant in the temperate climate zones. In $C_3$ plants, the primary $CO_2$ fixation or carboxylation reaction involves the enzyme ribulose-1,5-diphosphate carboxylase and the first stable product is a 3-carbon compound. $C_4$ plants, on the other hand, include such plants as tropical grasses, corn and sugar cane. In $C_4$ plants, an additional carboxylation reaction involving another enzyme, phosphoenol-pyruvate carboxylase, is the primary carboxylation reaction. The first stable carbon compound is a 4-carbon acid, which is subsequently decarboxylated. The $CO_2$ thus released is refixed by the $C_3$ cycle.

Both $C_4$ and $C_3$ plants exhibit a range of $^{13}C/^{12}C$ isotopic ratios, but typical values are ca. −10 to −14 per mil ($C_4$) and −21 to −26 per mil ($C_3$) (Weber et al., *J. Aqric. Food Chem.*, 45, 2942 (1997)). Coal and petroleum fall generally in this latter range. The $^{13}C$ measurement scale was originally defined by a zero set by pee dee belemnite (PDB) limestone, where values are given in parts per thousand deviations from this material. The "$\delta^{13}C$" values are in parts per thousand (per mil), abbreviated ‰, and are calculated as follows:

$$\delta^{13}C \equiv \frac{(^{13}C/^{12}C)\text{sample} - (^{13}C/^{12}C)\text{standard}}{(^{13}C/^{12}C)\text{standard}} \times 1000\text{‰}$$

Since the PDB reference material (RM) has been exhausted, a series of alternative RMs have been developed in cooperation with the IAEA, USGS, NIST, and other selected international isotope laboratories. Notations for the per mil deviations from PDB is $\delta^{13}C$. Measurements are made on $CO_2$ by high precision stable ratio mass spectrometry (IRMS) on molecular ions of masses 44, 45 and 46.

Biologically-derived 1,3-propanediol, and compositions comprising biologically-derived 1,3-propanediol, therefore, may be completely distinguished from their petrochemical derived counterparts on the basis of $^{14}C$ ($f_M$) and dual carbon-isotopic fingerprinting, indicating new compositions of matter. The ability to distinguish these products is beneficial in tracking these materials in commerce. For example, products comprising both "new" and "old" carbon isotope profiles may be distinguished from products made only of "old" materials. Hence, the instant materials may be followed in commerce on the basis of their unique profile and for the purposes of defining competition, for determining shelf life, and especially for assessing environmental impact.

Preferably the 1,3-propanediol used as the reactant or as a component of the reactant will have a purity of greater than about 99%, and more preferably greater than about 99.9%, by weight as determined by gas chromatographic analysis. Particularly preferred are the purified 1,3-propanediols as disclosed in US20040260125A1, US20040225161A1 and US20050069997A1, and polytrimethylene ether glycol made therefrom as disclosed in US20050020805A1.

The purified 1,3-propanediol preferably has the following characteristics:

(1) an ultraviolet absorption at 220 nm of less than about 0.200, and at 250 nm of less than about 0.075, and at 275 nm of less than about 0.075; and/or (2) a composition having CIELAB "b*" color value of less than about 0.15 (ASTM D6290), and an absorbance at 270 nm of less than about 0.075; and/or (3) a peroxide composition of less than about 10 ppm; and/or (4) a concentration of total organic impurities (organic compounds other than 1,3-propanediol) of less than about 400 ppm, more preferably less than about 300 ppm, and still more preferably less than about 150 ppm, as measured by gas chromatography.

The starting material for making polytrimethylene ether glycol depends on the desired polytrimethylene ether glycol, availability of starting materials, catalysts, equipment, etc., and comprises "1,3-propanediol reactant." By "1,3-propanediol reactant" is meant 1,3-propanediol, and oligomers and prepolymers of 1,3-propanediol preferably having a degree of polymerization of 2 to 9, and mixtures thereof. In some instances, it may be desirable to use up to 10% or more of low molecular weight oligomers where they are available. Thus, preferably the starting material comprises 1,3-propanediol and the dimer and trimer thereof. A particularly preferred starting material comprises about 90% by weight or more 1,3-propanediol, and more preferably 99% by weight or more 1,3-propanediol, based on the weight of the 1,3-propanediol reactant.

Polytrimethylene ether glycol can be made via a number of processes known in the art, such as disclosed in U.S. Pat. No. 6,977,291 and U.S. Pat. No. 6,720,459. A preferred process is as set forth in previously incorporated US20050020805A1.

As indicated above, polytrimethylene ether glycol may contain lesser amounts of other polyalkylene ether repeating units in addition to the trimethylene ether units. The monomers for use in preparing polytrimethylene ether glycol can, therefore, contain up to 50% by weight (preferably about 20 wt % or less, more preferably about 10 wt % or less, and still more preferably about 2 wt % or less), of comonomer diols in addition to the 1,3-propanediol reactant. Comonomer diols that are suitable for use in the process include aliphatic diols, for example, ethylene glycol, 1,6-hexanediol, 1,7-heptanediol, 1,8-octanediol, 1,9-nonanediol, 1,10-decanediol, 1,12-dodecanediol, 3,3,4,4,5,5-hexafluoro-1,5-pentanediol, 2,2,3,3,4,4,5,5-octafluoro-1,6-hexanediol, and 3,3,4,4,5,5,6,6,7,7,8,8,9,9,10,10-hexadecafluoro-1,12-dodecanediol; cycloaliphatic diols, for example, 1,4-cyclohexanediol, 1,4-cyclohexanedimethanol and isosorbide; and polyhydroxy compounds, for example, glycerol, trimethylolpropane, and pentaerythritol. A preferred group of comonomer diols is selected from the group consisting of ethylene glycol, 2-methyl-1,3-propanediol, 2,2-dimethyl-1,3-propanediol, 2,2-diethyl-1,3-propanediol, 2-ethyl-2-(hydroxymethyl)-1,3-propanediol, $C_6$-$C_{10}$ diols (such as 1,6-hexanediol, 1,8-octanediol and 1,10-decanediol) and isosorbide, and mixtures thereof. A particularly preferred diol other than 1,3-propanediol is ethylene glycol, and $C_6$-$C_{10}$ diols can be particularly useful as well.

One preferred polytrimethylene ether glycol containing comonomers is poly(trimethylene-co-ethylene ether) glycol such as described in US2004/0030095A1. Preferred poly(trimethylene-co-ethylene ether) glycols are prepared by acid catalyzed polycondensation of from 50 to about 99 mole % (preferably from about 60 to about 98 mole %, and more preferably from about 70 to about 98 mole %) 1,3-propanediol and up to 50 to about 1 mole % (preferably from about 40 to about 2 mole %, and more preferably from about 30 to about 2 mole %) ethylene glycol.

Polytrimethylene ether glycols useful in practicing this invention can contain small amounts of other repeat units, for example, from aliphatic or aromatic diacids or diesters, such as described in U.S. Pat. No. 6,608,168. This type of polytrimethylene ether glycol can also be called a "random polytrimethylene ether ester", and can be prepared by polycondensation of 1,3-propanediol reactant and about 10 to about 0.1 mole % of aliphatic or aromatic diacid or esters thereof, such as terephthalic acid, isophthalic acid, bibenzoic acid, naphthalic acid, bis(p-carboxyphenyl)methane, 1,5-naphthalene dicarboxylic acid, 2,6-naphthalene dicarboxylic acid, 2,7-naphthalene dicarboxylic acid, 4,4'-sulfonyl dibenzoic acid, p-(hydroxyethoxy)benzoic acid, and combinations thereof, and dimethyl terephthalate, bibenzoate, isophthlate, naphthalate and phthalate; and combinations thereof. Of these, terephthalic acid, dimethyl terephthalate and dimethyl isophthalate are preferred.

The polytrimethylene ether glycols preferred for use herein generally have a number average molecular weight from about 200 to about 3000, and preferably from about 200 to about 2000. In embodiments where a water-soluble polytrimethylene ether glycol is used, the number average molecular weight is preferably less than about 1000, more preferably from about 250 to about 950. The polytrimethylene ether glycols preferred for use herein are typically polydisperse polymers having a polydispersity of preferably from about 1.0 to about 2.2, more preferably from about 1.2 to about 2.0, and still more preferably from about 1.2 to about 1.8.

The polytrimethylene ether glycols for use in the present invention preferably have a color value of less than about 100 APHA, and more preferably less than about 50 APHA.

Polytrimethylene ether glycol as described above should in general have low acute oral toxicity, and not be a skin or eye irritant, or a skin sensitizer.

Mono- and Diesters of Polytrimethylene Ether Glycol (PO3G Esters)

The PO3G esters used in the present invention can be described as comprising one or more compounds of the formula (I):

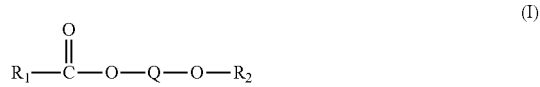

wherein Q represents the residue of a polytrimethylene ether glycol after abstraction of the hydroxyl groups, $R_2$ is H or $R_3CO$, and each of $R_1$ and $R_3$ is individually a substituted or unsubstituted aromatic, saturated aliphatic, unsaturated aliphatic or cycloaliphatic organic group, containing from 6 to 40 carbon atoms.

PO3G esters are preferably prepared by polycondensation of hydroxyl groups-containing monomers (monomers containing 2 or more hydroxyl groups) predominantly comprising 1,3-propanediol to form a PO3G (as disclosed in further detail below), followed by esterification with a monocarboxylic acid (or equivalent), as disclosed in previously incorporated U.S. application Ser. No. 11/593,954, filed Nov. 7, 2006, entitled "POLYTRIMETHYLENE ETHER GLYCOL ESTERS".

The PO3G ester thus prepared is a composition preferably comprising from about 50 to 100 wt %, more preferably from about 75 to 100 wt %, diester and from 0 to about 50 wt %, more preferably from 0 to about 25 wt %, monoester, based on the total weight of the esters. Preferably the mono- and diesters are esters of 2-ethylhexanoic acid, stearic acid, oleic acid, palmitic acid, linolenic acid and lauric acid. The deodorant compositions comprise about 0.5 wt % to about 10 wt %, and preferably between about 1 wt % and 8 wt %, emulsifiers/solubilizers (e.g poly(trimethylene ether)glycol ester (PO3G ester)).

The PO3G used for preparing the ester need not be the same as the PO3G co-component of the base fluid stock.

When the vehicle comprises the PO3G esters as described above, it is not necessary to add ethoxylated compounds. Thus, deodorant compositions which are substantially free of ethoxylated compounds (i.e., less than about 0.1 percent by weight of the total composition) can be produced. However, the presence of added ethoxylated compounds in deodorant compositions or vehicles. does not render such vehicles or compositions outside the scope of the invention.

Functional Ingredients

In most embodiments, the deodorant products of the invention comprise, in addition to polytrimethylene ether glycol, some functional ingredient which provides benefit to the user's body. Such materials are in general well-known to those persons of ordinary skill in the relevant personal care composition art, and may include moisturizing agents, antibacterials, and perfumes.

The functional ingredients (and other ingredients of the deodorant compositions as described below) can be categorized by the benefit they provide or by their postulated mode of action. However, it is to be understood that the functional ingredients (and other ingredients) useful herein can in some instances provide more than one benefit or operate via more than one mode of action. Therefore, classifications herein are made for the sake of convenience and are not intended to limit the active to that particular application or applications listed.

Examples of substances that may suitably be included in the deodorant products according to the present invention as functional ingredients include the following:

(1) perfumes and fragrances, which give rise to an olfactory response in the form of a fragrance, and deodorant perfumes which, in addition to providing a fragrance response, can also reduce body malodor;

(2) skin coolants, such as menthol, menthyl acetate, menthyl pyrrolidone carboxylate, N-ethyl-p-menthane-3-carboxamide and other derivatives of menthol, which give rise to a tactile response in the form of a cooling sensation on the skin;

(3) emollients, such as isopropylmyristate, mineral oils, vegetable oils, and glycerol/glycerine, which give rise to a tactile response in the form of an increase in skin lubricity;

(4) deodorant ingredients other than perfumes, whose function is to reduce the level of or eliminate micro flora at the skin surface, especially those responsible for the development of body malodor, including precursors of deodorants;

(5) moisturizing agents, that keep the skin moist by either adding moisture or preventing from evaporating from the skin;

(6) powders, pigments and colorants; and (7) medicinal agents.

Further examples of skin benefit agents include abrasives; absorbents; aesthetic components such as opacifying agents and pearlescent aids such as ethylene glycol distearate and $TiO_2$ coated mica; essential oils; skin sensates; cosmetic and drug astringents such as clove oil, menthol, camphor, eucalyptus oil, eugenol, menthyl lactate and witch hazel distillate; anti-acne agents such as resorcinol, sulfur, salicylic acid, benzoyl peroxide, erythromycin and zinc; anti-caking agents; antimicrobial agents such as iodopropyl butylcarbamate; antioxidants; cosmetic biocides; external analgesics; pH modifiers such as citric acid, sodium citrate, succinic acid, phosphoric acid, sodium hydroxide and sodium carbonate; skin soothing and/or healing agents such as panthenol and derivatives like ethyl panthenol, aloe vera, pantothenic acid and its derivatives, allantoin; bisabolol and dipotassium glycyrrhizinate; retinoids such as retinol palmitate); tocopheryl nicotinate; skin treating agents; vitamins and derivatives thereof; and other similar materials.

Humectants have been described as agents that control the moisture exchange between the product and air, both in the container and on the skin. Humectants have also been described as compounds that prevent drying of skin or that increase the water content of the top layers of skin (e.g., hygroscopic compounds).

Although polytrimethylene ether glycol is itself a useful humectant that has a strong tendency to retain water and forms gel in the absence of a gelling agent, it can also be used with other humectants or moisturizing agents, that: (a) facilitate hydration of the skin by inhibiting or preventing loss of water; (b) absorb water from the atmosphere and hydrate the skin; (c) enhance the ability of the skin to absorb water directly from the atmosphere; or (d) any combination thereof. Moisturizing agents also minimize or prevent the skin from drying and cracking.

Suitable moisturizing agents include hydrophobic agents, hydrophilic agents and combinations thereof. Examples of moisturizing agents are allantoin, glycerol, polyglycerylmethacrylate, panthenol, polyols, ceramide, borage oil (linoleic acid), tocopherol (Vitamin E), tocopherol linoleate, dimethicone, hyaluronic acid, sodium peroxylinecarbolic acid (sodium PCA), wheat protein (e.g., laurdimonium hydroxypropyl hydrolyzed wheat protein), hair keratin amino acids, panthenol; primrose oil; GLA 3 and other fish oils that may include, for example, the omega-3 and omega-6 oils and/or linoleic acid; and flax seed oil, and mixtures thereof. Other moisturizing agents can also be used.

Other Ingredients

In the case of the present invention, the polytrimethylene ether glycol and water function as the vehicle (or a component of the vehicle), or one or both the polytrimethylene ether glycol and the active ingredient are generally dissolved, suspended or emulsified into a vehicle of the types discussed above.

A variety of other ingredients, in addition to those already mentioned, may also be present in the deodorant compositions of the present invention. Examples of such other ingredients include gelling agents, surfactants, emulsifiers, and preservatives. Also, salts of fatty acids such as sodium or potassium salts of stearic, palmitic, oleic or linolenic acid, including mixtures thereof, can be present.

It is desirable that some or most of the ingredients in the deodorant compositions disclosed herein be derived from renewable sources. In preferred embodiments, the compositions comprise greater than about 70 percent renewably sourced ingredients, based on the total weight of the composition.

Cellulosic gums also can be used as additives in the compositions of this invention. For instance, US2003/0198616A1 describes a moisturizing skin gel wherein a water-soluble hydroxyalkylcellulose polymer typically performs a dual function of gelling the composition and forming a moisture barrier to reduce transepidermal water loss. Preferred cellulosic gums include water-soluble hydroxyalkylcellulose polymers such as hydroxymethylcellulose, hydroxyethylcellulose and hydroxypropylcellulose. Other thickening agents which have been used in skin-contacting compounds, include acacia, agar, alginate, carrageenan, gum tragacanth, xanthan gum, collagen, carboxypolymethylene, glyceryl monostearate, polyvinylpyrrolidone and polyacrylamide.

Surfactants may be used in the deodorant compositions of the invention. Typical surfactants are disclosed in US2003/0007939A1.

A vast number of personal care products are oil-in-water emulsions containing a dispersion of oil droplets in a continuous aqueous medium. Surfactants or emulsifiers are generally used to aid emulsification process of oil in water and to stabilize the thus formed emulsion against physical degradation processes. They are compounds that have hydrophobic and hydrophilic portions that act to reduce the surface tension of the aqueous solutions they are dissolved in. Although polytrimethylene ether glycol is easily dispersible in a continuous aqueous medium without adding any emulsifier or surfactant, additional emulsifiers may be used in many preferred embodiments of the invention. Most emulsifiers approved for cosmetic use can be used. Operable emulsifiers include nonionic, anionic, cationic, amphoteric or zwitterionic and blends thereof. Suitable emulsifiers are disclosed in U.S. Pat. No. 3,755,560 and U.S. Pat. No. 4,421,769. Examples are polyethylene glycol 20, sorbitan monolaurate (Polysorbate 20), polyethylene glycol 20 stearyl ether (Brij 78, Steareth 20), polyethylene glycol ether of lauryl alcohol (Laureth 23), polysorbate 80 (Tween 80), and lecithin. However, most of these surfactants are petroleum based, and it is preferred to replace with renewably sourced materials such as polytrimethyene ether glycol laurate of the present invention. Other commonly used ingredients in personal care compositions include preservatives, which may be selected from the many that are known in the art and commercially available.

Examples include benzyl alcohol, methyl paraben, propyl paraben, DMDM hydantoin, methylchloroisothiaoline, methylisothiazolinone, imidazolidinyl urea phenoxyethanol, sodium benzoate and benzoic acid. EDTA and salts thereof are often used to further enhance preservation.

The deodorant compositions as described herein comprise a carrier or vehicle composition in the range of about 10 wt % to about 95 wt % of the total deodorant composition, preferably between about 20 wt % and 90 wt %. Of this vehicle composition, about 5 wt % to about 85 wt %, preferably about 10 to about 70 wt %, is poly(trimethylene ether)glycol (PO3G). The vehicle generally comprises water, alcohol such as ethanol, isopropanol, diol such as 1,3-propanediol, 1,2-propanediol, polyol such as glycerin, sorbitol, xylitol, mannitol, maltitol and oils such as vegetable oils, or a combination thereof. It is desirable that at least some of such ingredients be derived from renewable sources.

As stated above, the deodorant compositions comprise about 0.5 wt % to about 10 wt %, preferably about 1 wt % to about 8 wt %, of a solidifying or gelling agent (e.g., sodium stearate). The deodorant compositions comprise about 0.5 wt % to about 10 wt %, and preferably between about 1 wt % and 8 wt %, emulsifiers/solubilizers (e.g poly(trimethylene ether) glycol ester (PO3G ester).

The deodorant compositions also generally comprise one or more functional additives, including fragrance, antibacterial agents (e.g. IRGASAN) and the like. Generally, fragrances will be included in amounts between about 0.1 wt % to about 3 wt %, and preferably between about 0.3 wt % and about 2.5 wt %. Fragrances can be selected from, for example, essential oils such as rosewood, lavender, lemon, lime, mandarin, rose, coriander, cypress, petitgrain, and pine. Antibacterial agents will be added in amounts between about 0.1 wt % and 1.5 wt %, preferably between about 0.2 wt % and 1.5 wt %. Examples of suitable antibacterial agents include Triclosan (5-chloro-2-(2,4-dichlorophenoxy)phenol), and CHLORACEL® sodium aluminum chlorhydroxy lactate (Reheis, Inc., Berkeley Heights, N.J.)

The deodorant compositions of this invention are readily prepared by use of conventional formulation and mixing techniques. Methods of making several personal care compositions using polytrimethylene ether glycol are described in the examples, which are exemplary only and not intended to be limiting.

Product Forms

Deodorant compositions or products are generally in the form of solid or gel sticks, creams, lotions, sprays etc. The compositions, thus, may be made into a wide variety of product types. These include but are not limited to, lotions, creams, gels, sticks, sprays, etc.

Most often deodorant products contain an active ingredient incorporated in a delivery vehicle. The desired effect of a deodorant product is achieved either by the deodorant active ingredients or by the vehicle itself at the site of application, in most cases on the skin or hair. With the aid of the vehicle, i.e. the vehicle acting as a carrier, the active ingredient is delivered to the application site where the desired effect is to be achieved.

The major types of deodorant vehicles most frequently fall into the following categories: (a) solutions; (b) emulsions, both oil-in-water and water-in-oil; and including lotions and creams; (c) suspensions; (d) gels; and (e) solids and semi-solids including stick products. Deodorant products in some vehicles, including liquids, gels, suspensions and emulsions, can be provided for application via roll-on applicator, as known in the art. A discussion of personal care and cosmetic vehicles is found in the previously incorporated *Handbook of Cosmetic Science and Technology*, Second Edition, edited by M Paye, A. O. Barel and H. I. Maibach, pages 99-123 (2005).

Solutions

Generally solutions used in personal care products are either based on aqueous or aqueous alcoholic media, or on inert oily materials. Most organic solvents are not suitable because of their local or systemic toxicity, which causes skin irritation or permeation into the body. Examples of solvents, in addition to water, that are frequently used in personal care compositions are polypropylene glycol, polyethylene glycol, ethanol, glycerol, ethylene glycol, 1,2,4-butanetriol, 1,2,6-hexanetriol, ethanol, isopropanol, butanetriol, sorbitol esters, butanediol, butylene glycol, hexylene glycol, methylpropanediol, pyrrolidone, N-methylpyrrolidone, dimethyl sulfoxide, dimethyl sulfone and similar solvents and mixtures thereof. Topical formulations containing such solvents are described in, for example, US2004/0105873A1.

Preferred are aqueous solutions. Polytrimethylene ether glycols suitable for aqueous solutions are either a homopolymer having molecular weight (Mn) of less than about 1000, or a water-soluble copolymer such as polytrimethylene-ethylene ether glycol having molecular weight of less than about 3000. Preferred solutions will generally comprise lower amounts of polytrimethylene ether glycol, typically from about 0.1 to about 10 wt % on the weight of the deodorant composition. Deodorant products are often formulated as solutions.

Gels

A "gel" in accordance with the present invention is a colloid in which the disperse phase has combined with the continuous phase to produce a viscous, jelly-like product.

Gels in accordance with the present invention can be aqueous or nonaqueous. The gels will typically comprise a vehicle comprising, in addition to the polytrimethylene glycol, a gelling agent such as described above. The vehicle of the gels will also typically comprise a solvent.

A preferred deodorant composition in accordance with this aspect of the present invention comprises an effective amount of at least one active personal care ingredient in a vehicle, wherein the vehicle is a gel comprising a gelling agent and from about 10 to about 70% by weight, based on the weight of the composition, of polytrimethylene ether glycol. Preferably, the vehicle comprises from about 30 to about 95% by weight, and more preferably from about 40 to about 80% by weight, based on the weight of the composition, of polytrimethylene ether glycol. The vehicle also preferably comprises a solvent, more preferably water. Deodorant compositions can be in gel form.

Polytrimethylene Ether Glycol/Water Gel

In one preferred embodiment, however, the gel is an aqueous gel comprising water and lower molecular weight polytrimethylene ether glycol, where the polytrimethylene glycol functions as the gelling agent, and is preferably the sole gelling agent. In this embodiment, the gel is preferably non-flowable at ambient temperature (e.g., at about 25° C. or below), and becomes a flowable liquid at a temperature of about 35° C. or higher and/or becomes a flowable liquid upon contact with human or animal skin.

The gelation behavior of polytrimethylene ether glycol in this embodiment is sensitive to molecular weight, comonomer amount and water level. Depending on the polymer molecular weight and its concentration, when added to water and mixed it can form an emulsion or a homogenous solution. Preferably, the polytrimethylene ether glycol should have a molecular weight (Mn) of less than about 1000, and should have a comonomer content of less than about 10 mole %.

Preferably, the polytrimethylene ether glycol is substantially a homopolymer of 1,3-propanediol.

These gel compositions are easily prepared by adding polytrimethylene ether glycol directly into water at ambient temperature. The order of addition, polymer to water or water to polymer, is not critical. No heating is required. The aqueous mixtures turn from a flowable fluid state to a non-flowable gel or creamy state within a few minutes. When the resulting gels are heated to a temperature above about 35° C., they return to their original flowable state but are able to gel again upon cooling. Thus, in use, the gels become a liquid upon contact with human or animal skin. As a result of this unique behavior of polytrimethylene ether glycol in water media, these lower molecular weight polytrimethylene ether glycols possess a unique combination of properties and can be used as a lubricant, surfactant, humectant, moisturizer and emollient.

Any other ingredients added to this gel composition, such as an active deodorant ingredient, are preferably added after gel formation.

This gelling behavior of the polytrimethylene ether glycol in aqueous systems is unusual in comparison, for example, to certain ethylene oxide and propylene oxide block copolymers show gelation behavior in water at high temperature but water-solubility at lower temperatures. For example, previously incorporated U.S. Pat. No. 5,256,396 discloses a composition comprising water and a water soluble, non-ionic block copolymer of ethylene oxide and propylene oxide. This composition is flowable at or below ambient temperature, but upon contact with the warm surface of an animal quickly forms a non-flowable gel. The polytrimethylene ether glycols exhibit the opposite behavior, forming a non-flowable gel at room temperature and turning into a flowable liquid upon contact with the warm surface of a human body.

The retention of water by polytrimethylene ether glycol by gel formation allows it to serve as an excellent moisturizing vehicle. This embodiment of the aqueous gel composition of the present invention is easily washed off with water from the substrate such as the skin or face. Agents such as ethylene/acrylic acid copolymers may be added to the compositions of the present invention to enhance their resistance to being washed off, if desired.

Emulsions

Emulsions are widely used as personal care vehicles. By "emulsion" is meant a stable mixture of two or more immiscible liquids held in suspension by small percentages of substances called emulsifiers, which may be nonionic, anionic, cationic or zwitterionic. In the case of oil-in-water emulsions, the oil phase is the internal or dispersed phase, and the water phase is the external (continuous) or carrier phase. In the case of water-in-oil emulsions, the water phase is the internal or dispersed phase, and the oil phase water is the external (continuous) or carrier phase.

If emulsions are liquid (flowable at ambient temperature), they are generally referred to as lotions. Creams are emulsions that occur in substantially non-flowable form (at ambient temperature). Generally creams do not flow through orifices under gravity because of their heavier consistency when compared to lotions. The consistency, or viscosity, of emulsions depends on several factors, including the ratio of internal to external phase, type of oil phase, and presence or absence of thickening agents in the continuous phase.

Two phase emulsion skin care preparations, such as lotions and creams, of the oil-in-water type and water-in-oil type are well-known in the cosmetic art and are useful in the subject invention. Triphase emulsion compositions, such as the water-in-oil-in-water type, as disclosed in U.S. Pat. No. 4,254,105, are also useful in the subject invention. In general, such triphase emulsions contain water, emollients and emulsifiers as essential ingredients. Oils useful in both types of emulsions, and also for solvents in solvent-based vehicles in general, include hydrocarbon oils and waxes (e.g., petrolatum, mineral oil, micro-crystalline waxes, polyalkenes, paraffins, cerasin, ozokerite, polyethylene, perhydrosqualene, poly alpha olefins, hydrogenated polyisobutenes and combinations thereof). Preferred are fatty acid derivatives, cholesterol, cholesterol derivatives, diglycerides and triglycerides (e.g., castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil, sesame oil, vegetable oils and vegetable oil derivatives, sunflower seed oil, coconut oil and derivatized coconut oil, cottonseed oil and derivatized cottonseed oil, jojoba oil, cocoa butter and combinations thereof, as well as any of the aforementioned oils that have been partially or fully hydrogenated), acetoglyceride esters (e.g., acetylated monoglycerides), alkyl esters, alkenyl esters (e.g., oleyl myristate, oleyl stearate, oleyl oleate, and combinations thereof), lanolin and its derivatives (e.g., lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol ricinoleate, hydroxylated lanolin, hydrogenated lanolin and combinations thereof), wax esters (e.g., beeswax and beeswax derivatives, spermaceti, myristyl myristate, stearyl stearate and combinations thereof), sterols and phospholipids, and combinations thereof. Examples of alkyl esters include isopropyl esters of fatty acids and long chain esters of long chain fatty acids, e.g., SEFA (sucrose esters of fatty acids), pentaerythritol esters, aromatic mono, di or triesters, cetyl ricinoleate, isopropyl palmitate, isopropyl myristate, cetyl ricinoleate and stearyl ricinoleate. Other examples include hexyl laurate, isohexyl laurate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof. Still other suitable oils include milk triglycerides (e.g., hydroxylated milk glyceride) and polyol fatty acid polyesters. Also useful are vegetable waxes such as carnauba and candelilla waxes; sterols such as cholesterol, cholesterol fatty acid esters; and phospholipids such as lecithin and derivatives, sphingo lipids, ceramides, glycosphingo lipids, and combinations thereof.

Suspensions

Still another aspect of the invention is a deodorant composition comprising a suspension. Suspensions consist of solid particles dispersed in a liquid or semi-solid medium. Sedimentation during storage is minimized by reducing particle size and/or by increasing the viscosity of the carrier phase. Typical uses of suspensions are essentially the same as those listed above for oil-in-water and water-in-oil emulsions.

Preferred suspensions comprise an effective amount of at least one solid active deodorant ingredient in a vehicle comprising from about 60 to about 90% by weight of polytrimethylene ether glycol, based on the weight of the deodorant composition. In one preferred embodiment, the vehicle comprises a solution of the polytrimethylene ether glycol and/or poltyrimethylene ether glycol ester in a solvent. In a preferred embodiment, the composition is a lotion or a cream.

Solids

Yet another aspect of the invention relates to a personal care composition comprising an effective amount of at least one active personal care ingredient, a solidifying agent, and from about 10 to about 90% by weight of polytrimethylene ether glycol based on the weight of the deodorant composition, wherein the composition is in the form of a solid or semi-solid at ambient temperature (e.g., 25° C. and below). Preferably, the composition comprises from about 10 to about 80% by weight, more preferably from about 20 to about 70% by weight, polytrimethylene ether glycol.

Solid delivery vehicles are generally cast in an elongated form as sticks. By rubbing the sticks onto the skin a variety of personal care ingredients can be delivered. Examples include deodorant sticks. There are several ways of achieving solid stick properties, such as mixtures of waxes and oils and solutions based on aqueous, propylene glycol and/or alcohol mixtures solidified usually by sodium stearate. Preferably, the solidifying agent is selected from the group consisting of a wax and sodium stearate. In preferred embodiments, the compositions described herein are substantially free from silicone-containing materials. "Substantially free" as used herein means less than about 0.1 weight percent silicone of the total deodorant composition.

Solid personal care products of the invention may also be finely divided and used in the form of powders.

Other Forms

It should be noted that most of the liquid vehicles described above can be in the form of foams, which are dispersions of gas in the liquid phase. The gas globules may be of any size, from colloidal to macroscopic, as in soap bubbles. Typical liquid foams are those used in shaving creams, etc.

Liquid or solid vehicle systems can also be applied as aerosols. By "aerosol" is meant a suspension of liquid or solid particles in a gas, the particles often being in the colloidal size range. Included are fine sprays (deodorants, etc.). Suspensions of various kinds are prepared by placing the components, together with a compressed gas, in a container (bomb). The pressure of the gas causes the mixture to be released as a fine spray (aerosol) when a valve is opened. Examples are perfumes, deodorants, shaving cream, and the like. The propellant gas may be, for example, a hydrocarbon (propane, isobutene), a chlorofluorocarbon, carbon dioxide or nitrous oxide.

EXAMPLES

Unless otherwise specified, the chemicals and reagents used in the examples below were used as obtained from Sigma-Aldrich Co., St. Louis, Mo.

ZEMEA™ 1,3-propanediol is available from DuPont Tate & Lyle Bio Products, Wilmington, Del.

IRGASAN™ is Ciba Specialty Chemical's brand name for triclosan.

The fragrance used was Lavender French Essential Oil from New Directions Aromatics, Inc., Toronto, Calif.

As used herein PEG means polyethylene glycol.

Water used in the examples below was distilled/deionized water.

Example 1

Synthesis of Poly(Trimethylene Ether)Glycol (PO3G Homopolymer)

A 22-L, 4-necked, round-bottomed flask, equipped with a nitrogen inlet, and a distillation head was charged with 11877 g of 1,3-propanediol. The liquid was sparged with nitrogen at a rate of 10 L/min. and mechanical stirring (using a stirring magnet driven by a magnetic stirrer below the flask) was done for about 15 min. After 15 min., 108 g of sulfuric acid was slowly added drop-wise from a separatory funnel through one of the ports over a period of at least 5 minutes. When this was finished, 15 g of 1,3-propanediol (PDO) was added to the separatory funnel and swirled to remove any residual sulfuric acid. This was added to the flask. The mixture was stirred and sparged as above and heated to 160° C. The water of reaction was removed by distillation and was collected continuously during the polymerization reaction. The reaction was continued for 14 hours, after which it was allowed to cool (while stirring and sparging were maintained) to 45° C.

The crude material was hydrolyzed as follows. The crude polymer was added to a 22-L, 5-necked, round-bottom flask, (equipped with a condenser and a mechanical mixer) along with an equal volume of distilled water. This mixture was stirred mechanically, sparged with nitrogen at a rate of about 150 mL/min. and heated to 100° C. It was allowed to reflux for 4 hours after which the heat was turned off and the mixture allowed to cool to 45° C. The stirring was discontinued and the sparging reduced to a minimum. Phase separation occurred during cooling. The aqueous phase water was removed and discarded. A volume of distilled water equal to the initial amount was added to the wet polymer remaining in the flask. Mixing, sparging and heating to 100° C. was done again for 1 hour after which the heat was turned off and the material allowed to cool as before. The aqueous phase was removed and discarded.

The residual sulfuric acid was determined by titration and neutralized with an excess of calcium hydroxide. The polymer was dried under reduced pressure at 90° C. for 3 hours and then filtered through a Whatman filter paper precoated with a CELPURE C-65 filter aid. The resulting PO3G had a number average molecular weight of 500. A 200 ppm of BHT, an antioxidant was added to this polymer.

Example 2

Synthesis of Poly(Trimethylene-Ethylene Ether)Glycol Copolymer

The above procedure described was repeated except for variation in the amounts of 1,3-propanediol (8811.2 g), 1,2-ethanediol (3080.8 g) and sulfuric acid (108 g) and the reaction time to 25 hours to obtain a poly(trimethylene-ethylene ether) glycol copolymer having a number average molecular weight (Mn) of 890. A 200 ppm of BHT, an antioxidant was added to this polymer.

Example 3

Synthesis of a 2-Ethylhexanoate Ester of Polytrimethylene Ether Glycol 1,3-propanediol, 125 g was charged into a 500 mL flask fitted with a stirrer, a condenser and an inlet for nitrogen. The liquid in the flask was flushed with dry nitrogen and 0.62 g of concentrated sulfuric acid was added. The reaction temperature was raised to 170° C. and the reaction was allowed to proceed at 170° C. for 160 min. Then the temperature was raised to 180° C. and held at 180° C. for 3 hours.

The reaction mixture was cooled to 110° C. and 70.95 g of 2-ethylhexanoic acid (99%) was added. The reaction temperature was then raised to 120° C. under nitrogen flow with continuous agitation at 180 rpm and maintained at that temperature for 4 h. Then heating was stopped and the product was allowed to cool to room temperature.

The 25 g of obtained product was mixed with 100 g of 1 wt % sodium hydroxide solution, the mixture was thoroughly agitated and transferred to separating funnel. The aqueous layer was removed, 100 mL of water was added to product, thoroughly agitated and the aqueous layer was removed. The later step was repeated one more time. The product was dried at 90° C. using a rotovap. The product had a molecular weight of 385. The obtained product was used in formulations in the Examples below.

Example 4

Synthesis of a Laurate Ester of Polytrimethylene Ether Glycol 1,3-propanediol, 1504.5 g was charged into a 5 L flask fitted with a stirrer, a condenser and an inlet for nitrogen. The liquid in the flask was flushed with dry nitrogen and heated to 170° C. After temperature reached to 170° C., 7.8 g of concentrated sulfuric acid was added. The reaction was allowed to continue for 3 h. The reaction temperature was raised to 180° C. and the reaction was allowed to proceed 2 h 20 min.

305 g of obtained product was mixed with 400 g of lauric acid and 3.5 g of concentrated sulfuric acid in a 2 L flask fitted with a stirrer, a condenser and an inlet for nitrogen. The reaction temperature was raised to 140° C. Then reaction was continued for 15 min at 140° C., 55 min at 150° C. and 45 min at 165° C. Then the product was cooled.

450 g of obtained product was mixed with 955 g of 5 wt % sodium carbonate solution, and heated to 70° C. while stirring under nitrogen flow. After 30 min., the product was transferred to a separating funnel. The aqueous layer was removed. The product was dried at 90° C. using a rotovap. The product had a molecular weight of 640. The obtained product was used in formulations in the Examples below.

Deodorants with Polytrimethylene Ether Glycol of Example 1

The deodorant formulations described in the examples below consist of functional ingredients (IRGASAN and Fragrance), a vehicle polytrimethylene ether glycol (PO3G) and water, and other ingredients such as PEG monolaurate (solubilizer) and sodium stearate (solidifying agent).

Stability of the deodorants made in the examples below was determined by visual inspection. Stable formulations did not appreciably soften, expand or shrink at the temperatures listed with each example for at least 30 days. Stability can also be determined by thermal analysis techniques, e.g., differential scanning calorimetry.

Example 5-6

Sodium stearate, Polytrimethylene ether glycol, PEG monolaurate, and water were charged into a 250 mL flask fitted with a stirrer and blended. The blended mixture was heated to 90° C. while stirring at 180 rpm. After the solids were completely melted and a clear solution was formed, the temperature was reduced to 80° C. and triclosan was added. After 10 min the fragrance was added. Heating was stopped and the product was transferred into a container while cooling. The transferred product was allowed to cool to room temperature. The product of example 5 was stable at 45° C. and the product of example 6 was stable at 40° C.

| Ingredients | Example 5 | Example 6 |
|---|---|---|
| Sodium stearate, % | 6.5 | 10 |
| Poly(trimethylene ether) glycol, % | 60 | 40 |
| PEG monolaurate, % | 2.0 | 2.0 |
| Water, % | 31.0 | 47.5 |
| IRGASAN ™ Triclosan, % | 0.2 | 0.2 |
| Fragrance, % | 0.3 | 0.3 |

Example 7

6.5 g of sodium stearate, 30 g of poly(trimethylene ether) glycol, 30 g of ZEMEA™, 2.0 g of PEG monolaurate, and 31.0 g of water were charged into a 250 mL flask fitted with a stirrer and blended. The blended mixture was heated to 90° C. while stirring at 180 rpm. After the solids were completely melted and a clear solution was formed, the temperature was reduced to 80° C. and 0.2 g of triclosan was added. After 10 min fragrance was added. Heating was stopped and the product was transferred into a container while cooling. The transferred product was allowed to cool to room temperature. The product was stable at 45° C. The vehicle composition of this deodorant had 34.0 wt % of poly(trimethylene ether) glycol.

| Ingredients | Wt % |
|---|---|
| Sodium stearate | 6.5 |
| Poly(trimethylene ether) glycol | 30.0 |
| ZEMEA ™ | 30.0 |
| PEG monolaurate | 2.0 |
| Water | 31.0 |
| IRGASAN ™ Triclosan, | 0.2 |
| Fragrance | 0.3 |

Example 8

6.5 g of sodium stearate, 12 g of poly(trimethylene ether) glycol, 50 g of ZEMEA™, and 31.0 g of water were charged into a 250 mL flask fitted with a stirrer and blended. The blended mixture was heated to 90° C. while stirring at 180 rpm. After solids were completely melted and a clear solution was formed, the temperature was reduced to 80° C. and 0.2 g of triclosan was added. After 10 min fragrance was added. Heating was stopped and the product was transferred into a container while cooling. The transferred product was allowed to cool to room temperature. The product was stable at 45° C. The vehicle composition of this deodorant had 12.9 wt % of poly(trimethylene ether) glycol.

| Ingredients | Wt % |
|---|---|
| Sodium stearate | 6.5 |
| Poly(trimethylene ether) glycol | 12.0 |
| ZEMEA ™ | 50.0 |
| Water | 31.0 |
| IRGASAN ™ Triclosan | 0.2 |
| Fragrance | 0.3 |

Examples 9-11

Deodorants Comprising Polytrimethylene Ether Glycol Ester(S) (Non-Ethoxylated)

Example 9

6.5 g of sodium stearate, 60.0 g of ZEMEA™, 2.0 g of poly(trimethylene ether) glycol ester (as made according to example 3 above), and 31.0 g of water were charged into a 250 mL flask fitted with a stirrer and blended. The blended mixture was heated to 90° C. while stirring at 180 rpm. After solids were completely melted and a clear solution was formed, the temperature was reduced to 80° C. and 0.2 g of triclosan was added. After 10 min fragrance was added. Heating was stopped and the product was transferred into container while cooling. The transferred product was allowed to cool to room temperature. The product was stable at 45° C. The deodorant had 2 wt % of poly(trimethylene ether) glycol 2-ethylhexanoate.

| Ingredients | Wt % |
| --- | --- |
| Sodium stearate | 6.5 |
| ZEMEA ™ | 60 |
| Poly(trimethylene ether) glycol 2-ethylhexanoate | 2.0 |
| Water | 31.0 |
| IRGASAN ™ Triclosan | 0.2 |
| Fragrance | 0.3 |

Example 10

6.5 g of sodium stearate, 50.0 g of ZEMEA™, 10.0 g of poly(trimethylene ether) glycol, 2.0 g of poly(trimethylene ether) glycol 2-ethylhexanoate of example 3, and 31.0 g of water were charged into a 250 mL flask fitted with a stirrer and blended. The blended mixture was heated to 90° C. while stirring at 180 rpm. After the solids were completely melted and a clear solution was formed, the temperature was reduced to 80° C. and 0.2 g of triclosan was added. After 10 min fragrance was added. Heating was stopped and the product was transferred into a container while cooling. The transferred product was allowed to cool to room temperature. The product was stable at 45° C. The vehicle composition of this deodorant has 11 wt % of poly(trimethylene ether) glycol and the deodorant composition had 2 wt % of poly(trimethylene ether) glycol 2-ethylhexanoate.

| Ingredients | Wt % |
| --- | --- |
| Sodium stearate | 6.5 |
| ZEMEA ™ | 50.0 |
| Poly(trimethylene ether) glycol | 10.0 |
| Poly(trimethylene ether) glycol 2-ethylhexanoate | 2.0 |
| Water | 31.0 |
| IRGASAN ™ Triclosan | 0.2 |
| Fragrance | 0.3 |

Example 11

6.5 g of sodium stearate, 50.0 g of ZEMEA™, 10.0 g of poly(trimethylene ether) glycol of example 1, 2.0 g of poly(trimethylene ether) glycol laurate of example 4, and 31.0 g of water were charged into a 250 mL flask fitted with a stirrer and blended. The blended mixture was heated to 90° C. while stirring at 180 rpm. After the solids were completely melted and a clear solution was formed, the temperature was reduced to 80° C. and 0.2 g of triclosan was added. After 10 min fragrance was added. Heating was stopped and the product was transferred into container while cooling. The transferred product was allowed to cool to room temperature. The product was stable at 45° C. The vehicle composition of this deodorant has 11 wt % of poly(trimethylene ether) glycol and the deodorant has 2 wt % of poly(trimethylene ether) glycol laurate.

| Ingredients | Wt % |
| --- | --- |
| Sodium stearate | 6.5 |
| ZEMEA ™ | 50.0 |
| Poly(trimethylene ether) glycol | 10.0 |
| Poly(trimethylene ether) glycol laurate | 2.0 |
| Water | 31.0 |
| IRGASAN ™ Triclosan | 0.2 |
| Fragrance | 0.3 |

Example 12

6.5 g of sodium stearate, 60.0 g of poly(trimethylene-ethylene ether) glycol copolymer of example 2, 2.0 g of PEG monolaurate, and 31.0 g of water were charged into a 250 mL flask fitted with a stirrer and blended. The blended mixture was heated to 90° C. while stirring at 180 rpm. After the solids were completely melted and a clear solution was formed, the temperature was reduced to 80° C. and 0.2 g of triclosan was added. After 10 min fragrance was added. Heating was stopped and the product was transferred into container while cooling. The transferred product was allowed to cool to room temperature. The product was stable at 45° C. The vehicle composition of this deodorant had 65.9 wt % of poly(trimethylene ether) glycol copolyol.

| Ingredients | Wt % |
| --- | --- |
| Sodium stearate | 6.5 |
| Poly(trimethylene-ethylene ether) glycol | 60.0 |
| PEG monolaurate | 2.0 |
| Water | 31.0 |
| IRGASAN ™ Triclosan | 0.2 |
| Fragrance | 0.3 |

What is claimed is:

1. A deodorant composition comprising an effective amount of at least one active deodorant ingredient in a vehicle, wherein the vehicle comprises polytrimethylene ether glycol.

2. A deodorant composition according to claim 1 wherein the vehicle further comprises one or more renewably sourced materials selected from: water, ethanol, butanol, 1,3-propanediol, glycerine, 1,2-propylene glycol, sorbitol, xylitol, mannitol, maltitol and vegetable oils.

3. The deodorant composition of claim 1, wherein said vehicle comprises from about 5 to 85 percent by weight, based on the weight of the vehicle, of polytrimethylene ether glycol.

4. The deodorant composition of claim 1, wherein said vehicle comprises from about 10 to 70 percent by weight, based on the weight of the vehicle, of polytrimethylene ether glycol.

5. The deodorant composition of claim 1, wherein the polytrimethylene ether glycol has a number average molecular weight of 200 to 3000.

6. The deodorant composition of claim 1, wherein said composition contains less than about 0.1 weight percent silicone based on the total deodorant composition.

7. The deodorant composition of claim 1, further comprising polytrimethylene ether glycol ester.

8. The deodorant composition of claim 7, where in the composition comprises from 0.1 to 10% by weight, based on the total weight of the composition, of polytrimethylene ether glycol ester.

9. The deodorant composition of claim 1, wherein said composition further comprises one or more of
 (a) sodium or potassium salts of fatty acids;
 (b) fragrances
 (c) antibacterial agents; and
 (d) colorants.

10. The deodorant composition of claim 1, comprising greater than about 70 percent renewably sourced ingredients, based on the total weight of the composition.

11. The deodorant composition of claim 2, wherein the amount of one or more renewably sourced materials is from about 15 to 95 percent by weight, based on the weight of the vehicle.

12. The deodorant composition of claim 9, further comprising one or more polytrimethylene ether glycols and/or polytrimethylene ether glycol ester(s).

13. The deodorant composition of claim 11, wherein said composition is contains less than about 0.1 weight percent silicone based on the total deodorant composition.

14. The deodorant composition of claim 13, wherein said composition further comprises one or more of:
 (a) sodium or potassium salts of fatty acids;
 (b) fragrances
 (c) antibacterial agents; and
 (d) colorants.

15. The deodorant composition of claim 1 or 11 in a form selected from the group consisting of solid and gels sticks, creams, lotions, liquids and sprays.

16. The deodorant composition of claim 11, comprising greater than about 70 percent renewably sourced ingredients, based on the total weight of the composition.

* * * * *